(12) United States Patent
Huang et al.

(10) Patent No.: US 8,088,940 B2
(45) Date of Patent: Jan. 3, 2012

(54) HYDROLYZABLE SILANES OF LOW VOC-GENERATING POTENTIAL AND RESINOUS COMPOSITIONS CONTAINING SAME

(75) Inventors: Misty W. Huang, New City, NY (US); Antonio Chaves, Chappaqua, NY (US); Bruce A. Waldman, Cortlandt Manor, NY (US); Shayne J. Landon, Ballston Lake, NY (US)

(73) Assignee: Momentive Performance Materials Inc., Albany, NY (US)

( * ) Notice: Subject to any disclaimer, the term of this patent is extended or adjusted under 35 U.S.C. 154(b) by 932 days.

(21) Appl. No.: 11/731,577

(22) Filed: Mar. 30, 2007

(65) Prior Publication Data

US 2008/0237537 A1    Oct. 2, 2008

(51) Int. Cl.
*C07F 7/08* (2006.01)
*C08L 9/00* (2006.01)

(52) U.S. Cl. ............... 556/464; 556/407; 556/410

(58) Field of Classification Search .............. None
See application file for complete search history.

(56) References Cited

U.S. PATENT DOCUMENTS

| | | | | |
|---|---|---|---|---|
| 5,998,504 | A * | 12/1999 | Groth et al. | 523/213 |
| 6,319,311 | B1 * | 11/2001 | Katz et al. | 106/287.11 |
| 6,440,876 | B1 * | 8/2002 | Wang et al. | 438/778 |
| 2005/0245753 | A1 | 11/2005 | Cruse et al. | |
| 2005/0277774 | A1 * | 12/2005 | Seong et al. | 546/14 |
| 2006/0036034 | A1 | 2/2006 | Chaves et al. | |
| 2006/0177657 | A1 | 8/2006 | Weller | |
| 2006/0178451 | A1 | 8/2006 | Weller | |
| 2006/0178487 | A1 | 8/2006 | Weller | |
| 2006/0205907 | A1 | 9/2006 | Guyer | |
| 2006/0293480 | A1 | 12/2006 | Landon et al. | |

FOREIGN PATENT DOCUMENTS

WO    WO2006/023785 A    3/2006

OTHER PUBLICATIONS

U.S. Appl. No. 11/358,550, filed Feb. 21, 2006, Chaves et al.
U.S. Appl. No. 11/358,818, filed Feb. 21, 2006, Chaves et al.
U.S. Appl. No. 11/358,369, filed Feb. 21, 2006, Chaves et al.
U.S. Appl. No. 11/358,861, filed Feb. 21, 2006, Chaves et al.
U.S. Appl. No. 11/505,221, filed Aug. 14, 2006, Chaves et al.
U.S. Appl. No. 11/505,166, filed Aug. 14, 2006, Chaves et al.
U.S. Appl. No. 11/505,055, filed Aug. 14, 2006, Chaves et al.
U.S. Appl. No. 11/505,178, filed Aug. 14, 2006, Chaves et al.
U.S. Appl. No. 11/544,132, filed Oct. 6, 2006, Chaves et al.
U.S. Appl. No. 11/544,142, filed Oct. 6, 2006, Chaves et al.
U.S. Appl. No. 11/598,906, filed Nov. 14, 2006, Pohl.

* cited by examiner

*Primary Examiner* — Daniel Sullivan
*Assistant Examiner* — Yevegeny Valenrod
(74) *Attorney, Agent, or Firm* — Dominick G. Vicari; Joseph S. Ostroff

(57) ABSTRACT

In accordance with the present invention, a hydrolyzable silane of low VOC-generating potential is provided which possesses:
  (i) at least one organofunctional group, said group being a non-bulky electron-withdrawing group and/or a group which interacts with an organic resin, the organofunctional group being bonded to a silicon atom of a hydrolyzable silyl group through a stable bridging groups; and
  (ii) at least one hydrolyzable group bonded to silicon and containing at least two heteroatoms selected from the group consisting of oxygen, nitrogen and their combinations, hydrolysis of the hydrolyzable group generating a compound having a vapor pressure lower than 0.1 mm Hg at 20° C.

Further in accordance with the invention, a resinous composition of low VOC-generating potential is provided which comprises:
  a) a resinous composition property-enhancing amount of at least one hydrolyzable silane of low VOC-generating potential which possesses:
    (i) at least one organofunctional group, said group being a non-bulky electron-withdrawing group and/or a group which interacts with an organic resin (b), the organofunctional group being bonded to a silicon atom of a hydrolyzable silyl group through a stable bridging group, and
    (ii) at least one hydrolyzable group bonded to silicon and containing at least two heteroatoms selected from the group consisting of oxygen, nitrogen and their combinations, hydrolysis of the hydrolyzable group generating a compound having a vapor pressure lower than 0.1 mm Hg at 20° C.; and,
  b) at least one organic resin containing at least one group capable of reacting with organofunctional group (i) of hydrolyzable silane (a) and/or with water.

19 Claims, No Drawings

HYDROLYZABLE SILANES OF LOW VOC-GENERATING POTENTIAL AND RESINOUS COMPOSITIONS CONTAINING SAME

BACKGROUND OF THE INVENTION (1) Field of the Invention

This invention relates to hydrolyzable silanes which on hydrolysis generate byproducts having low vapor pressure (LVP) and to resinous compositions, e.g., organic resin-containing adhesives, sealants and coatings, incorporating such silanes.

(2) Description of Related Art

Conventional hydrolyzable organofunctional silanes are known for use as adhesion promoters, crosslinkers, surface modifiers and moisture scavengers (desiccants) in adhesive, sealant and coating compositions. These silanes are characterized by possessing one or more hydrolyzable methoxy or ethoxy groups that, in the presence of moisture, undergo hydrolysis and subsequent condensation to form stable silicon-oxygen-silicon or silicon-oxygen-metal bonds. Hydrolysis of these conventional hydrolyzable organofunctional silanes generates high vapor pressure byproducts such as methanol or ethanol. These volatile byproducts are undesirable for many types of consumer products due to concerns about exposing consumers to volatile organic compounds (VOCs). VOC emissions from consumer products have been, and continue to be, the subject of governmental regulation such as the State of California Air Resources Board's Regulation for Reducing Volatile Organic Compound Emissions from Consumer Products, Final Regulation Order, Subchapter 8.5, Consumer Products.

Following the manufacture of moisture curable resins, it is highly desirable that the resins be shielded from moisture so as to minimize any hydrolysis that might negatively affect the usefulness of products containing them Moisture curable resins if exposed to even small amounts of moisture at any time following their production and before the use of products containing them will experience some degree of premature curing ranging from negligible to excessive. The need to avoid a deleterious degree of premature curing of such resins can be readily appreciated, e.g., in the case of a moisture curable sealant which is packaged in a moisture-resistant cylindrical container. The sealant is discharged from the cylindrical container onto a substrate when and as desired by application of moderate force exerted by a hand-actuated piston. Exposure of the sealant to even small amounts of moisture while still in its container, e.g., the amounts of moisture that may be present in the sealant at the time of its packaging, initiates cure, resulting in an increase in the viscosity of the sealant and requiring an unduly high degree of force for its discharge from the container. This build-up of product viscosity over time, viewed as a storage stability problem, if not anticipated and suitably addressed can be a major drawback to the convenient and successful application of these products.

It has therefore been a practice to include a moisture scavenger in a moisture curable sealant, coating, adhesive or silane-containing resin component thereof in order to reduce the possibility or extent of such in-storage hydrolysis and subsequent condensation of the silane thereby conserving or increasing its storage stability. Among the moisture scavengers known in the art are vinyltrimethoxysilane and methyltrimethoxysilane. These compounds preferentially react with moisture thereby reducing the opportunity for excessive premature curing of the silane-containing organic resin component of the composition. However, upon application of the silane resin-containing composition, a conventional moisture scavenging vinyltrimethoxysilane or methyltrimethoxysilane component will also undergo hydrolysis and condensation producing significant amounts of volatile organic compounds (VOCs), specifically, monoalcohols such as methanol, an environmental safety hazard which continues to be the target of corrective legislation and administrative rule making.

Another common practice in the manufacture of coatings, adhesives and sealants is to incorporate into their formulations an adhesion-enhancing amount of a typically low molecular weight silane such as an aminosilane, ureido silane or epoxysilane. These hydrolyzable organofunctional silanes form bonds with the organic resin and the substrate onto which they are applied. As in the case of moisture scavenging vinyltrimethoxysilanes, adhesion-promoting silanes will also emit significant amounts of VOCs such as methanol and ethanol when undergoing hydrolysis which occurs upon application of compositions containing these hydrolyzable organofunctional silanes to the substrate.

BRIEF SUMMARY OF THE INVENTION

In accordance with the present invention, a hydrolyzable silane of low VOC-generating potential is provided which possesses:

(i) at least one organofunctional group, said group being a non-bulky electron-withdrawing group and/or a group which is capable of interacting with a mutually interactive organic resin following contact therewith, the organofunctional group being bonded to a silicon atom of a hydrolyzable silyl group through a stable bridging group, and (ii) at least one hydrolyzable group bonded to silicon and containing at least two heteroatoms selected from the group consisting of oxygen, nitrogen and their combinations, hydrolysis of the hydrolyzable group generating a compound having a vapor pressure lower than 0.1 mm Hg at 20° C.

Further in accordance with the invention, a resinous composition of low VOC-generating potential is provided which comprises:

a) a resinous composition property-enhancing amount of at least one hydrolyzable silane which possesses:
  (i) at least one organofunctional group, said group being a non-bulky electron-withdrawing group and/or a group which is capable of interacting with a mutually interactive organic resin following contact therewith, the organofunctional group being bonded to a silicon atom of a hydrolyzable silyl group through a stable bridging group, and
  (ii) at least one hydrolyzable group bonded to silicon and containing at least two heteroatoms selected from the group consisting of oxygen, nitrogen and their combinations, hydrolysis of the hydrolyzable group generating a compound having a vapor pressure lower than 0.1 mm Hg at 20° C.; and, b) at least one organic resin which is interactive with organofunctional group (i) of hydrolyzable silane (a) and/or with water.

Organofunctional group (i) of hydrolyzable silane (a) confers upon the silane the ability to enhance one or more of the functional properties of a composition containing organic resin (b), e.g., the storage stability and/or adhesion strength of the composition. While silane (a) will also undergo hydrolysis and condensation upon exposure to moisture which occurs during the curing of the composition, hydrolyzable group (ii)

of the silane upon undergoing hydrolysis will generate a non-volatile organic compound (non-VOC), or low vapor pressure volatile organic compound (LVP-VOC), e.g., a glycol or other polyhydric alcohol of relatively high boiling point and/or low vapor pressure, thus eliminating or reducing the amounts of VOCs compared to those generated during the hydrolysis of known moisture scavenging silanes and adhesion promoting silanes.

The expression of "non-bulky electron withdrawing group" shall be understood herein to designate an organofunctional group and the bridging group to which it is chemically bonded possessing a σ* (Taft polar substituent constant) of 0 or greater and an $E_s$ (Taft steric substituent constant) of −0.40 or greater. See in this regard, "Rates of Equilibrium of Organic Reactions" by John E. Zeffler and Ernest Grunwald, pp. 218-231, John Wiley and Sons, Inc., New York (1963), the entire contents of which are incorporated by reference herein.

The expression "group which is capable of interacting with a mutually interactive organic resin", which is an additional or alternative characteristic of organofunctional group (i) of silane (a), shall be understood herein to designate a group which forms covalent or ionic bonds with a mutually interactive organic resin or causes physical entanglement with the resin as a result of hydrogen bonding or van der Waals interactions therewith.

The expression "non-VOC or LVP-VOC compound" designates a chemical compound having a boiling point of greater than 216° C. as determined by ASTM D 86-96, or having a vapor pressure of less than 0.1 mm Hg at 20° C. as determined by ARB Method 310.

The expression "resinous composition property-enhancing" refers to at least one property of a resinous composition of the invention, e.g., its storage stability, its adhesion strength, its durability, the dispersibility of its filler component(s) if present, one or more of its mechanical properties, e.g., tensile strength, elongation, tear strength, etc., which is enhanced or improved by the presence within the composition of hydrolyzable silane (a).

DETAILED DESCRIPTION OF THE INVENTION

Hydrolyzable silane (a) can be monomeric or oligomeric and may contain numerous species of both types.

In one embodiment, hydrolyzable silane (a) is at least one monomeric silane of general Formula (1):

$$(X^1{}_a X^2{}_b X^3{}_c SiR^1)_d Z \quad (1)$$

wherein:

each occurrence of $R^1$ is independently a chemical bond between a silicon atom and a carbon atom of the Z group; a hydrocarbyl group of 1 to 10 carbon atoms; or a heterocarbyl of 1 to 10 carbon atoms and at least one heteroatom of nitrogen or oxygen;

each occurrence of $X^1$ is a monovalent alkyl or aryl group of from 1 to 6 carbon atoms or a monovalent heterocarbyl group of from 2 to 8 carbon atoms and at least two heteroatom selected from the group consisting of oxygen and nitrogen, with the proviso that one heteroatom is bonded to a carbon atom of the heterocarbyl group and to the silicon atom;

each occurrence of $X^2$ is a divalent heterocarbyl group of from 2 to 8 carbon atoms and at least two heteroatoms selected from the group consisting of oxygen and nitrogen, with the proviso that two heteroatoms are bonded to two different carbon atoms of the heterocarbyl group and to the same silicon atom;

each occurrence of $X^3$ is a trivalent heterocarbyl group of from about 3 to 8 carbons and at least three heteroatoms selected from the group consisting of oxygen and nitrogen, with the proviso that three heteroatoms are bonded to three different carbon atoms of the heterocarbyl group and to the same silicon atom;

each Z is a monovalent or polyvalent organofunctional group of valence d selected from the group consisting of hydrogen, amino, carbamato, epoxy, ureido and alkenyl groups, provided, where Z does not possess a carbon atom, $R^1$ cannot be a chemical bond; and, each occurrence of a, b, c and d are integers, wherein a is 0 to 3; b is 0 or 1; c is 0 or 1; and d is 1 to 4; with the proviso that when c is 0, then a+2b=3 and when b is 1, then a=1 and c=0.

As used herein in connection with hydrolyzable silane (a), the term, "hydrocarbyl", refers to a monovalent or polyvalent hydrocarbon; "heterocarbyl", refers to a monovalent or polyvalent hydrocarbyl group that contains at least one heteroatom atom selected from the group consisting of nitrogen and oxygen; "alkyl" includes straight, branched and cyclic alkyl groups; "alkenyl" includes any straight, branched, or cyclic alkenyl group containing one or more carbon-carbon double bonds, where the site of substitution can be either at a carbon-carbon double bond or elsewhere in the group; "aryl" includes any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents. The hydrocarbyl group can contain unsaturation, such as carbon-carbon double or triple bonds. The heteroatom is inserted in between two carbon atoms or in between a carbon atom and a hydrogen atom. The heterocarbyl group can contain unsaturation, such as carbon-carbon, carbon-nitrogen or carbon-oxygen double bonds or carbon-carbon or carbon-nitrogen triple bonds.

The $X^1$ group can be represented by $R^2$ wherein $R^2$ is an alkyl or an aryl group of 1 to 6 carbon atom, or by general Formula (2):

$$(HA^1)_{e-1} R^3 (A^2-) \quad (2)$$

wherein $R^3$ is a hydrocarbyl group of 2 to 8 carbon atoms; each occurrence of $A^1$ and $A^2$ is a heteroatom selected from the group consisting of oxygen and nitrogen of the structure —$NR^4$—, wherein each occurrence of $R^4$ is a hydrogen or an alkyl or aryl group of from 1 to 6 carbon atoms; and e is an integer from 2 to 3. The $A^2$ group is bonded to a carbon atom of $R^3$ and to the silicon atom of Formula (1). $A^1$ is bonded to $R^3$ and to a hydrogen atom. The group $HA^1$- represents a free hydroxyl (—OH) or amino (—$NR^4H$) group and is therefore not covalently bonded directly to the silicon atom.

The $X^2$ group can be represented by general Formula (3):

$$(HA^3)_{f-2} R^5 (A^4-)_2 \quad (3)$$

wherein $R^5$ is a hydrocarbyl group of 2 to 8 carbon atoms; each occurrence of $A^3$ and $A^4$ is a heteroatom selected from the group consisting of oxygen and substituted nitrogen of the structure —$NR^4$—, wherein each occurrence of $R^4$ is a hydrogen or an alkyl or aryl group of from 1 to 6 carbon atoms; and f is an integer from 2 to 3. The two -$A^4$- groups are bonded to two different carbon atom of $R^5$ and to the same silicon atom of Formula (1) to form a cyclic structure. $A^3$ is bonded to $R^5$ and to a hydrogen atom. The group $HA^3$- represents a free hydroxyl (—OH) or amino (—$NR^4H$) groups and is therefore not covalently bonded directly to the silicon atom.

The $X^3$ group can be represented by general Formula (4):

$$R^6(A^5-)_3 \quad (4)$$

wherein $R^6$ is a hydrocarbyl group of 3 to 8 carbon atoms; each occurrence of $A^5$ is a heteroatom selected from the group consisting of oxygen and substituted nitrogen of the structure —$NR^4$— wherein each occurrence of $R^4$ is a hydrogen or an alkyl or aryl group of from 1 to 6 carbon atoms. The three -$A^5$- groups are bonded to three different carbon atoms of $R^6$ and to the same silicon atom of Formula (1) to form a bicyclic structure.

The Z groups can be represented by hydrogen or by general Formula (5):

$$(—)_g N(R^7)_{3-g}[—R^8 N(R^9)_{2-h}(—)_h]_i \quad (5)$$

wherein each occurrence of $R^7$ and $R^9$ is independently hydrogen or an alkyl or aryl group of from 1 to 6 carbon atoms; $R^8$ is an alkylene, aralkylene or arylene group of from 2 to 10 carbon atoms; (—) represents the bond between the nitrogen atom and a carbon of the $R^1$ group; each g, h and i are integers wherein g is from 0 to 3, h is from 1 to 2 and i is 0 or 1 with the provisos that (i) g+(i×h)=d; (ii) when g=3, then i=0; and (iii) when g=0, then i=1;
or by general Formula (6):

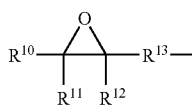

(6)

wherein:

each occurrence of $R^{10}$ is independently a hydrogen or an alkyl group containing from 1 to 6 carbon atoms;

each occurrence of $R^{11}$ is independently a hydrogen or a hydrocarbyl group containing from 1 to 10 carbon atoms and, optionally, at least one oxygen atom, selected from the group consisting of monovalent alkyl, alkenyl, arenyl, aryl and aralkyl groups; divalent alkylene, alkenylene, arenylene, arylene and aralkylene groups in which one carbon atom of $R^{11}$ is covalently bonded to a carbon of the epoxy ring and the same or different carbon atom of $R^{11}$ is covalently bonded to a carbon atom of $R^{12}$ or $R^{13}$ to form a cyclic aliphatic structure; and polyvalent hydrocarbyl in which one carbon atom of $R^1$ is covalently bonded to a carbon atom of the epoxy ring and the same and/or different carbon atom of $R^2$ forms at least two covalent bonds with carbon atoms of $R^{12}$ or $R^{13}$ or at least one covalent bond with both $R^{12}$ and $R^{13}$ to form a bicyclic or a polycyclic aliphatic structure;

each occurrence of $R^{12}$ is independently a hydrogen or a hydrocarbyl group containing from 1 to 10 carbon atoms and, optionally, at least one oxygen atom, selected from the group consisting of monovalent alkyl, alkenyl, arenyl, aryl and aralkyl groups; divalent alkylene, alkenylene, arenylene, arylene and aralkylene groups in which one carbon atom of $R^{12}$ is covalently bonded to a carbon atom of the epoxy ring and the same or different carbon atom of $R^{12}$ is covalently bonded to a carbon atom of $R^{11}$ or $R^{13}$ to form a cyclic aliphatic structure; and polyvalent hydrocarbyl in which one carbon atom of $R^{12}$ is covalently bonded to a carbon atom of the epoxy ring and the same and/or different carbon atoms of $R^{12}$ form at least two covalent bonds with $R^{11}$ or $R^{13}$ or at least one covalent bond with both $R^{11}$ and $R^{13}$ to form a bicyclic or a polycyclic aliphatic structure;

each occurrence of $R^{13}$ is independently a chemical bond between the epoxy ring and $R^1$; a divalent or polyvalent hydrocarbyl group containing up to 12 carbon atoms selected from the group consisting of divalent alkylene, aralkylene, arenylene, arylene and aralkylene groups linking the epoxy group to $R^1$ and, optionally, at least one oxygen atom; and polyvalent hydrocarbyl group in which one carbon atom of $R^{13}$ forms a covalent bond with the carbon atom of the epoxy ring, the same or different carbon atom of $R^{13}$ forms a bond with a carbon atom of $R^1$, and the same or different carbon atom of $R^{13}$ forms at least one covalent bond with a carbon atom of $R^{11}$ or $R^{12}$ to form a bicyclic or a polycyclic structure;
or by general Formula (7):

$$(—)_j N(R^{14})_{2-j} C(=O)N(R^{15})_{2-k}(—)_k \quad (7)$$

wherein each occurrence of $R^{14}$ and $R^{15}$ is independently a hydrogen or an alkyl or aryl group of from 1 to 6 carbon atoms; (—) represents the bond between the nitrogen atom and a carbon of the $R^1$ group; j and k are an integers wherein j is from 1 to 2, k is from 0 to 2 with the proviso that j+k=d;
or by general Formula (8):

wherein each occurrence of $R^{16}$, $R^{17}$ and $R^{18}$ is independently a hydrogen or an alkyl or aryl group of from 1 to 6 carbon atoms; and (—) represents the bond between the unsaturated carbon atom and a carbon of the $R^1$ group or the silicon atom;
or by general Formula (9):

$$R^{19}OC(=O)NH— \quad (9)$$

wherein $R^{19}$ is a hydrocarbyl group of from 1 to 8 carbon atoms.

In another embodiment, silane (a) is at least one oligomeric silane of general Formula (10):

$$[(X^1_a X^2_b X^b_n SiR^1)_d Z]_m \quad (10)$$

wherein:

each occurrence of $R^1$ is independently a chemical bond; a hydrocarbyl group of 1 to 10 carbon atoms; or a heterocarbyl of 1 to 10 carbon atoms and at least one heteroatom of nitrogen or oxygen;

each occurrence of $X^1$ is a monovalent alkyl or aryl group of from about 1 to 6 carbon atoms or a monovalent heterocarbyl group of from about 2 to 8 carbon atoms and at least two heteroatom selected from the group consisting of oxygen and nitrogen, with the proviso that one heteroatom is bonded to a carbon atom of the heterocarbyl group of $X^1$ and to the silicon atom;

each occurrence of $X^2$ is a divalent heterocarbyl group of from about 2 to 8 carbon atoms and at least two heteroatoms selected from the group consisting of oxygen and nitrogen, with the proviso that two heteroatoms are bonded to two different carbon atoms of the heterocarbyl group of $X^2$ and to the same silicon atom to form a cyclic structure;

each occurrence of $X^b$ is independently at least a divalent heterocarbyl group of from about 2 to about 8 carbon atoms and at least two heteroatoms selected from the group consisting of oxygen and nitrogen, with the proviso that one heteroatom is bonded to a carbon atom of the heterocarbyl group of $X^b$ and to the silicon atom and that the second heteroatom is bonded to a different carbon atom of the heterocarbyl group of $X^b$ and a different silicon atom; and specifically $X^b$ is represented by general Formula (11):

$$(HA^6)_{2-o}R^{20}(A^7-)(A^8-)_o \qquad (11)$$

wherein:
$R^{20}$ is a hydrocarbyl group of 2 to 8 carbon atoms; each occurrence of $A^6$, $A^7$ and $A^8$ is a heteroatom selected from the group consisting of oxygen and substituted nitrogen of the structure —$NR^4$— wherein each occurrence of $R^4$ is hydrogen or an alkyl or aryl group of from 1 to 6 carbon atoms; and o is an integer from 1 to 2, with the proviso that $A^7$ and $A^8$ are bonded to different carbon atoms of $R^{20}$ and to silicon atoms on different monomer units;

each Z is a monovalent or polyvalent organofunctional group of valence d selected from the group consisting of hydrogen, amino, epoxy, ureido and alkenyl groups; and, each occurrence of a, b, d, n, m and o is independently an integer, wherein a is 0 to 2; b is 0 or 1; d is 1 to 4; m is 2 to 10, n is 1 to 3; o is 1 to 2; with the proviso that when b is 1, then a is 0 and n is 1

Examples of organofunctional group (i) of hydrolyzable silane (a) that are non-bulky electron-withdrawing groups include vinyl and methyl.

Examples of organofunctional group (i) of hydrolyzable silane (a) that are interactive with mutually interactive resin (b) include amino, carbamato, epoxy, ureido, alkenyl, and the like.

In one embodiment of the present invention, silane (a) is represented by general Formula (1):

$$(X^1_a X^2_b X^3_c SiR^1)_d Z \qquad (1)$$

wherein:
$R^1$ is a straight chain alkylene group of from 1 to 3, and preferably 3, carbon atoms;
$X^1$ is a methyl group or a group represented by general Formula (2):

$$(HA^1)_{e-1}R^3(A^2-) \qquad (2)$$

wherein $R^3$ is a hydrocarbyl group of 3 to 6 carbon atoms; each occurrence of $A^1$ and $A^2$ is oxygen and e is 1 or 2;

$X^2$ group can be represented by general Formula (3):

$$(HA^3)_{f-2}R^5(A^4-)_2 \qquad (3)$$

wherein $R^5$ is a hydrocarbyl group of 3 to 6 carbon atoms; each occurrence of $A^3$ and $A^4$ is oxygen and f is 2 or 3;

$X^3$ group can be represented by general Formula (4):

$$R^6(A^5-)_3 \qquad (4)$$

wherein $R^6$ is a hydrocarbyl group of 3 to 6 carbon atoms; each occurrence of $A^5$ is oxygen;

Z is —$NH_2$, —$NHR^8NH_2$ wherein $R^8$ is ethylene, propylene or butylene, —$NHC(=O)NH_2$ or glycidoxy; and, a, b and c have the aforestated meanings and d is 1.

In another embodiment of the present invention, silane (a) is represented by Formula (10):

$$[(X^1_a X^2_b X^b_n SiR^1)_d Z]_m \qquad (10)$$

wherein:
$R^1$ is a straight chain alkylene group of from 1 to 3 and preferably 3, carbon atoms;
$X^1$ is a methyl group or a group represented by the general Formula (2):

$$(HA^1)_{e-1}R^3(A^2-) \qquad (2)$$

wherein $R^3$ is a hydrocarbyl group of 3 to 6 carbon atoms; each occurrence of $A^1$ and $A^2$ is oxygen and e is 1 or 2;

$X^2$ group can be represented by the general Formula (3):

$$(HA^3)_{f-2}R^5(A^4-)_2 \qquad (3)$$

wherein $R^5$ is a hydrocarbyl group of 3 to 6 carbon atoms; each occurrence of $A^3$ and $A^4$ is oxygen; and f is 2 or 3;

$X^b$ group can be represented by the general Formula (11):

$$(HA^6)_{2-o}R^{20}(A^7-)(A^8-)_o \qquad (10)$$

wherein $R^{20}$ is a hydrocarbyl group of 3 to 6 carbon atoms; each occurrence of $A^6$, $A^7$ and $A^8$ is oxygen; and o is an integer from 1 to 2, with the proviso that $A^7$ and $A^8$ are bonded to different carbon atom of the $R^{20}$ and to silicon atoms on different monomer units;

Z is —$NH_2$, —$NHR^8NH_2$, wherein $R^8$ is ethylene, propylene or butylene, —$NHC(=O)NH_2$, and glycidoxy; and, a, b, and n have the aforestated meaning; d is 1; and m is 2 to 5.

In yet another embodiment, hydrolyzable silane (a) is a mixture of monomeric silane(s) of Formula (1) and oligomeric silane(s) of Formula (10) wherein the amount of monomer(s) can range from about 1 to about 50 weight percent, preferably from about 5 to about 35 weight percent and more preferably from about 10 to about 25 weight percent, and the amount of oligomer(s) can range from about 50 to about 99 weight percent, preferably from about 65 to about 95 weight percent and more preferably from about 75 to about 90 weight percent.

Representative non-limiting examples of hydrolyzable silane (a) include 3-(2-aminomethyl-5-methyl-[1,3,2]dioxasilinan-2-yloxy)-2-methyl-propan-1-ol; 3-(2-aminopropyl-5-methyl-[1,3,2]dioxasilinan-2-yloxy)-2-methyl-propan-1-ol; C-(2,5-dimethyl-[1,3,2]dioxasilinan-2-yl)-methylamine; C-(2,5-dimethyl-[1,3,2]dioxasilinan-2-yl)-propylamine; 4-[2-(3-amino-propyl)-4,4,6-trimethyl-[1,3,2]dioxasilinan-2-yloxy]-2-methyl-pentan-2-ol; 3-{2-[3-(2-amino-ethylamino)-propyl]-4-methyl-[1,3,2]dioxasilinan-2-yloxy}-butan-1-ol; C-{2-[3-(2-aminomethyl-5-methyl-[1,3,2]dioxasilinan-2-yloxy)-2-methyl-propoxy]-5-methyl-[1,3,2]dioxasilinan-2-yl}-methylamine; 3-(2-{3-[2-(3-amino-propyl)-5-methyl-[1,3,2]dioxasilinan-2-yloxy]-2-methyl-propoxy}-5-methyl-[1,3,2]dioxasilinan-2-yl)-propylamine; {3-[2-(3-hydroxy-1-methyl-propoxy)-4-methyl-[1,3,2]dioxasilinan-2-yl]-propyl}-urea; {3-[2-(3-hydroxy-1-methyl-propoxy)-4-methyl-[1,3,2]dioxasilinan-2-yl]-propyl}-urea; [2-(3-hydroxy-2-methyl-propoxy)-5-methyl-[1,3,2]dioxasilinan-2-ylmethyl]-urea; [3-(5-methyl-2-{2-methyl-3-[5-methyl-2-(3-ureido-propyl)-[1,3,2]dioxasilinan-2-yloxy]-propoxy}-[1,3,2]dioxasilinan-2-yl)-propyl]-urea; 2-methyl-3-(5-methyl-2-vinyl-[1,3,2]dioxasilinan-2-yloxy)-propan-1-ol; 2-methyl-acrylic acid 2-[2-(3-hydroxy-2-methyl-propoxy)-5-methyl-[1,3,2]dioxasilinan-2-yl]-ethyl ester; 2-methyl-3-[5-methyl-2-(2-oxiranylmethoxy-ethyl)-[1,3,2]dioxasilinan-2-yloxy]-propan-1-ol; 2,5-dimethyl-2-(2-oxiranylmethoxy-ethyl)-[1,3,2]dioxasilinane; 2,4,4,6-tetramethyl-2-(2-oxiranylmethoxy-ethyl)-[1,3,2]dioxasilinane; 2,2,4,4,6-pentamethyl-[1,3,2]dioxasilinane; 2,2,4,4,6-pentamethyl-[1,3,2]dioxasilinane; 2-[5-methyl-2-(6-methyl-5-methylene-hept-6-enyl)-[1,3,2]dioxasilinan-2-yloxy]-propan-1-ol; and the like.

Representative examples of mixtures of hydrolyzable silane (a) include the following:

(1) from about 20 to about 30 weight percent 3-(2-aminomethyl-5-methyl-[1,3,2]dioxasilinan-2-yloxy)-2-methyl-propan-1-ol and, correspondingly, from about 70 to about 80 weight percent C-{2-[3-(2-aminomethyl-5-methyl-[1,3,2]dioxasilinan-2-yloxy)-2-methyl-propoxy]-5-methyl-[1,3,2]dioxasilinan-2-yl}-methylamine;

(2) from about 10 to about 10 weight percent 3-(2-aminopropyl-5-methyl-[1,3,2]dioxasilinan-2-yloxy)-2-methyl-propan-1-ol and, correspondingly, from about 80 to about 90 weight percent 3-(2-{3-[2-(3-amino-propyl)-5-methyl-[1,3,2]dioxasilinan-2-yloxy]-2-methyl-propoxy}-5-methyl-[1,3,2]dioxasilinan-2-yl)-propylamine;

(3) from about 40 to about 55 weight percent {3-[2-(3-hydroxy-1-methyl-propoxy)-4-methyl-[1,3,2]dioxasilinan-2-yl]-propyl}-urea and, correspondingly, from about 45 to about 60 weight percent [3-(5-methyl-2-{2-methyl-3-[5-methyl-2-(3-ureido-propyl)-[1,3,2]dioxasilinan-2-yloxy]-propoxy}-[1,3,2]dioxasilinan-2-yl)-propyl]-urea; and, (4) from about 5 to about 15 weight percent 3-(2-aminomethyl-5-methyl-[1,3,2]dioxasilinan-2-yloxy)-2-methyl-propan-1-ol and, correspondingly, from about 85 to 95 weight percent 2,2,4,4,6-pentamethyl-[1,3,2]dioxasilinane.

Hydrolyzable silane (a) and mixtures thereof can be readily obtained in good yield by the reaction of at least one silane of general Formula (12):

$$(X^4X^5X^6SiR^1)_dZ \quad (12)$$

wherein, $R^1$, $Z$ and $d$ have the aforestated meanings;

each $X^4$ is a monovalent group selected from the group consisting of $R^2$, wherein $R^2$ is an alkyl or aryl group of from about 1 to 6 carbon atoms; halo, including Cl—, Br— or I—; —$NR^{21}_2$, wherein each occurrence of $R^{21}$ is hydrogen or an alkyl group of from 1 to 6 carbon atoms or acyloxy; and $R^{22}O$—, wherein $R^{22}$ is an alkyl group of from 1 to 6 carbon atom; and each $X^5$ and $X^6$ is a monovalent group selected from the group consisting of halo, including Cl—, Br— or I—; —$NR^{21}_2$, wherein each occurrence of $R^{21}$ is hydrogen or an alkyl group of from 1 to 6 carbon atoms or acyloxy; and $R^{22}O$—, wherein $R^{22}$ is an alkyl group of from 1 to 6 carbon atom;

with at least one reactant of general Formula (13):

$$(HA^1)_eR^3(A^2H) \quad (13)$$

wherein $R^3$ is a hydrocarbyl group of 2 to 8 carbon atoms; each occurrence of $A^1$ and $A^2$ is a heteroatom selected from the group consisting of oxygen and nitrogen of the structure —$NR^4$—, wherein each occurrence of $R^4$ is a hydrogen or an alkyl or aryl group of from 1 to 6 carbon atoms; and $e$ is an integer of from 1 to 2. This reaction produces a quantity of volatile byproduct, e.g., hydrogen chloride, dimethyl amine or methanol, which can be readily recovered during the manufacturing operation and, if desired, used in synthesis, e.g., in the production of silanes of Formula (12). For a detailed description of the foregoing process for manufacturing hydrolyzable silane (a), reference may be made to U.S. Pat. No. 6,489,500 and published U.S. patent application 2006 0036034, the entire contents of which are incorporated by reference herein.

When undergoing hydrolysis, silane (a) will release nonvolatile organic species $(HA^1)_eR^3(A^2H)$, supra, thus greatly reducing or even eliminating the evolution of volatile monoalcohols such as methanol or ethanol, and in doing so, reduce or eliminate the environmental hazards associated with such VOCs.

Organic resin (b) in the composition of the invention is mutually interactive with organofunctional group (i) of hydrolyzable silane (a) and/or with moisture. Representative organic resins (b) include those polymers containing a reactive organofunctional group selected from the group consisting of hydroxyl (—OH), carboxyl (—C(=O)OH), isocyanato (—N=C=O), thioisocyanato (—N=C=S), carbamato (—C(=O)NH—), ureido (—NHC(=O)NH—), amido (—C(=O)NH—), halo (Cl—, Br— and I—), epoxy

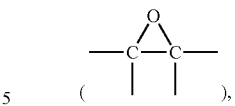

episulfide

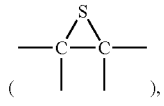

amino (—NH—), mercapto (—SH) and hydrolyzable silyl group of the formula —$SiX^7X^8X^9$ wherein $X^7$ is independently selected from the group consisting of $R^{23}O$—, $R^{23}C(=O)O$—, $R^{23}_2C=NO$—, $R^{23}_2C=CR^{23}O$— and $R^{23}_2NO$— wherein each $R^{23}$ is independently selected from the group consisting of hydrogen and alkyl, alkenyl, arenyl, aryl and aralkyl groups of up to 18 carbon atoms, optionally containing at least one oxygen or sulfur atom; and each occurrence of $X^8$ and $X^9$ is independently selected from the group consisting of $R^{23}O$—, $R^{23}C(=O)O$—, $R^{23}_2C=NO$—, $R^{23}_2NO$—, $R^{23}_2C=CR^{23}O$— and $R^{23}$ wherein $R^{23}$ has the aforestated definition.

Representative examples of organic resin (b) include phenolic, epoxy, such as anhydride cured epoxy and amine cured epoxy, polyester, polyamide, polyurethane, polyphenylene sulfide, polycarbonate, polyacrylate, polymethacrylate, polyvinyl alcohol, polyacrylamide, polymethacrylamide, polyvinyl chloride, polyvinylidene chloride, silane-terminated polyol such as those derived from polyether polyols, polyester polyols and hydrogenated and non-hydrogenated polyalkadiene diols, silane-terminated polyurethane, silylated polyolefin and polystyrene resins and resins obtained from the copolymerization of two or more ethylenically unsaturated monomers such as acrylates, methacrylates, vinyl alcohol, vinyl acetate, alkenes, styrene, vinyl chloride, vinylidene chloride, acrolein, acrylonitrile, acrylic acid, methacrylic acid, ethylenically unsaturated silanes, and the like.

For a composition of low VOC-generating potential of the present invention which contains a moisture curable organic resin (b), the composition can contain a moisture scavenging amount of at least one silane (a) which increases its shelf-stability. Suitable moisture-curable resins (b) include silane-containing resins, cyanoacrylates, isocyanate-terminated polyurethanes, ionic resins and epoxy resins all of which are known for use in adhesives, sealants and/or coatings. Particularly useful organofunctional groups (i) of silane (a) are methyl and vinyl.

Silane-containing resins are especially useful for formulating adhesive, sealant or coating compositions in accordance with the invention. Illustrative of such resins are silane-containing polysiloxanes, silylated resins and silane-containing copolymers derived from the copolymerization of at least one ethylenically unsaturated silane and at least one other ethylenically unsaturated comonomer.

Silane-containing organic resins (b) include silane-terminated polydimethylsiloxanes, silylated polyols, silylated polyethers, silylated polyurethane resins and silane-containing copolymers derived from the copolymerization of one or more ethylenically unsaturated silanes, such as vinylsilanes, allylsilanes and methallylsilanes, acryloxyalkylsilane, methacryloxyalkylsilanes and one or more other ethylenically unsaturated monomers such as olefinic hydrocarbons, acrylic acid, methacrylic acid, acrylate ester, methacrylate ester, ethylenically unsaturated dicarboxylic acids and/or their anhydrides, oligomers and/or polymers possessing ethylenic unsaturation, and the like.

Useful silylated polyols include those prepared by the reaction of a polyol, preferably a polymeric diol or triol, and an isocyanatosilane. The polyol can be, e.g., a polyether polyol, polyester polyol, polyetherester polyol, polyesterether polyol or hydroxyl-terminated polybutadiene, in particular, a hydrogenated polybutadiene diol, or mixtures thereof. Especially preferred are polyether diols possessing low terminal unsaturation, e.g., on the order of from about 0.018 to about 0.20 meq/g, and number average molecular weights of from about 5,000 to about 100,000, obtained by oxyalkylating a difunctional initiator with ethylene oxide, propylene oxide or mixtures thereof employing a double metal cyanide (DMC) catalyst. Useful isocyanatosilanes for silylating these and other polyols include isocyanatopropyltrimethoxysilane, isocyanatoisopropyltrimethoxsilane, isocyanato-n-butyltrimethoxsilane, isocyanato-t-butyltrimethoxysilane, isocyanatopropyltriethoxysilane, isocyanatoisopropyltriethoxysilane, isocyanato-n-butyltriethoxysilane, isocyanato-t-butyltriethoxysilane, isocyanatomethanyltrimethoxysilane; isocyanatomethanyltriethoxysilane, isocyanatomethanylmethyldimethoxysilane, isocyanatomethanylmethyldiethoxysilane, and the like, as well as mixtures thereof Useful silylated polyurethane resins include those obtained from the end-capping of isocyanate-terminated polyurethane prepolymers and hydroxyl-terminated polyurethane prepolymers with hydrolyzable silyl groups.

The first type of silylated polyurethane resin can be produced by reacting an isocyanate-terminated polyurethane prepolymer, itself obtained from the reaction of a stoichiometric excess of organic polyisocyanate with a polyol such as any of those aforementioned, and preferably from the reaction of a diisocyanate such as isophorone diisocyanate (IPDI) with a polyether diol such as any of those aforementioned, with a silane possessing functionality that is reactive for the isocyanate group, in particular, secondary amine or mercapto functionality. Useful silanes include secondary aminosilanes such as N-methylaminopropyltrimethoxysilane, N-ethylaminoproyltrimethoxysilane, N-methylaminoisobutyltrimethoxysilane, N-methylaminopropyltrimethoxysilane, N-methylaminobutyltriethoxysilane, N-methylaminopropylmethoxydiethoxysilane, N-methylaminopropyldimethylmethoxysilane, N-methylaminobutylethyldiethoxsilane; N-methylaminobutyldiethylethoxysilane, N,N-bis[3-trimethoxysilyl)propyl]amine, N,N-bisp3-triethoxysilyl)propyl]amine, N,N-bis[3-triethoxysilyl)butyl]amine, and the like, and mercaptosilanes such as gamma-mercaptopropylmethyldimethoxysilane, gamma-mercaptopropyltrimethoxysilane, gamma-mercaptopropylmethyldiethoxysilane, gamma-mercaptopropyltriethoxysilane, gamma-mercaptopropylethyldimethoxilane, gama-mercaptopropylethyldiethoxysilane, beta-mercaptopropydimethylmethoxsilane, beta-mercaptoethylmethyldimethoxysilane, beta-mercaptoethyltriethoxysilane, and the like. Mixtures of these and similar silanes can, of course, also be employed as silylating reactants.

Low VOC silane-containing polymers are disclosed in U.S. patent application Ser. No. 11/290,045, filed on Dec. 1, 2005, the entire contents of which are incorporated by entirety herein.

The second type of silylated polyurethane resin can be produced by reacting a hydroxyl-terminated polyurethane prepolymer, itself obtained from the reaction of a stoichiometric excess of polyol with a polyisocyanate, and advantageously from the reaction of a polyether diol such as any of those aforementioned with a diisocyanate such as isophorone diisocyanate, with an isocyanatosilane such as any of those mentioned above.

Yet another type of silane-containing resin that is useful as resin (b) in the composition of the invention is represented by general Formula (14):

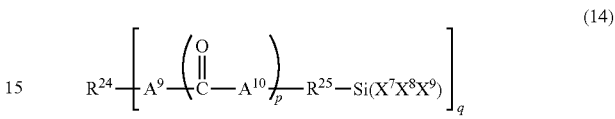

(14)

wherein:

$R^{24}$ is a monovalent or polyvalent organic polymer fragment having an number average molecular weight of from about 500 to about 25,000 grams/mole;

each occurrence of $R^{25}$ is independently a divalent hydrocarbyl group containing from 1 to 12 carbon atoms selected from the group consisting of divalent alkylene, alkenylene, arenylene, arylene and aralkylene, and, optionally, contains at least one heteroatom selected from the group consisting of oxygen, nitrogen and sulfur;

each occurrence of $A^9$ is independently selected from divalent oxygen (—O—), sulfur (—S—) or substituted nitrogen of the structure $(-)_2NR^{26}$, wherein $R^{26}$ is hydrogen, alkyl, alkenyl, arenyl, aryl, aralkyl or —$R^{25}SiX^7X^8X^9$ group, wherein each $R^3$, other than hydrogen, contains from 1 to 18 carbon atoms, and with the provisos that when $A^9$ is oxygen or sulfur, then $A^{10}$ is $(-)_2NR^{26}$ and when p is 0, then $A^9$ is oxygen;

each occurrence of $A^{10}$ is independently selected from divalent oxygen (—O—), sulfur (—S—) or substituted nitrogen of the structure $(-)_2NR^{26}$, wherein $R^{26}$ is hydrogen, alkyl, alkenyl, arenyl, aryl, aralkyl or —$R^{25}SiX^7X^8X^9$ group, wherein each $R^{26}$, other than hydrogen, contains from 1 to 18 carbon atoms, and with the provisos that when $A^{10}$ is oxygen or sulfur, then $A^9$ is $(-)_2NR^{26}$;

each occurrence of $X^7$ is independently selected from the group consisting of $R^{23}O—$, $R^{23}C(=O)O—$, $R^{23}_2C=NO—$, $R^{23}_2C=CR^{23}O—$, and $R^{23}_2NO—$ wherein each $R^{23}$ is independently selected from the group consisting of hydrogen, alkyl, alkenyl, arenyl, aryl, and aralkyl groups, wherein each $R^{23}$, other than hydrogen, contains from 1 to 18 carbon atoms, and, optionally, contains at least one oxygen or sulfur atom;

each occurrence of $X^8$ and $X^9$ is independently selected from the group consisting of $R^{23}O—$, $R^{23}C(=O)O—$, $R^{23}_2C=NO—$, $R^{23}_2C=CR^{23}O—$, $R^{23}_2NO—$ and $R^{23}$ wherein each $R^{23}$ is independently selected from the group consisting of hydrogen, alkyl, alkenyl, arenyl, aryl, and aralkyl groups, wherein each $R^{23}$, other than hydrogen, contains from 1 to 18 carbon atoms and, optionally, contains at least one oxygen or sulfur atom; and, each occurrence of subscripts p and q is independently an integer wherein p is 0 or 1 and q is 1 to 6.

For further details regarding the silane-containing resin of Formula (14), reference may be made to pending commonly assigned Huang et al. U.S. patent application Ser. No. 11/715, 000, filed Mar. 7, 2007, entitled "Moisture-Curable Silylated Polymer Resin Composition," the entire contents of which are incorporated by reference herein.

When formulated as an adhesive, sealant or coating, the composition of the present invention can additionally contain one or more other optional components that are known in the art such as, e.g., filler, UV stabilizer, antioxidant, catalyst, cure accelerator, thixotropic agent, plasticizer, pigment, dye, surfactant, solvent and biocide.

Silane (a) is added to organic resin (b) and other additional components using mixing processes known in the art and including mixing with a planetary mixer, a homogenizer, mechanical stirrer, extruder and the like. Generally, the silane (a) is added to the organic resin (b), before the other additional components are added, especially if the organic resin (b) is reactive with water. Silane (a) was remove any excess water from the organic resin (b) and from the additional components as they are subsequently added, and thereby increase the shelf-stability of the formulated adhesive, sealant and coating composition. Silane (a) also aids in the dispersion of the filler, pigments and other particulate components.

Of the total weight of hydrolyzable silane (a) and organic resin (b) in the resinous composition of the invention, silane (a) can, e.g., be present at a level of from about 0.05 to about 5 weight percent preferably from about 0.1 to about 3 weight percent, and more preferably from about 0.5 to about 1.5 weight percent, with organic resin (b) representing the balance of the combined weight of these two materials.

Typical fillers suitable for the present invention include, for example, reinforcing fillers such as fumed silica, precipitated silica and calcium carbonates and the like. The plasticizers suitable for the present invention can be to modify the properties and to facilitate use of higher filler levels. Exemplary plasticizers include phthalates, diproplyene and diethylene glycol dibenzoates, alkylsulphonate phenols, alkyl phenathres, alkyl/diaryl phosphates and mixtures thereof and the like. The adhesive, sealant or coating composition of the present invention can include various thixotropic or anti-sagging agents. Various castor waxes, fumed silica, treated clays and polyamides typify this class of additives. Stabilizers can be incorporated into composition of this invention include, for example, hindered amine and dialkydydroxyamine. Suitable cure catalysts for timely curing (crosslinking) of the silane-containing organic resin composition can be achieved with the use of various metal complexes of tin, titanium, zirconium and the like.

The silane-containing organic resin composition of the present invention can include other additives typically employed for coating, adhesive and sealant applications. These additives would include solvents, pigments or other colorants, dyes, surfactant, fungicides and biocides. Such components may be employed in conventional amounts. Coating formulations would include additives as described for moisture-curable silylated polymer resin composition, though in different proportions than sealant or adhesive formulations, and typically include solvents and defoamers as examples.

A better understanding of the present invention and of its many advantages will be had by referring to the following specific examples, given by way of illustration.

EXAMPLE 1

This example illustrates the preparation of a silane (a) or mixture thereof, useful as a moisture scavenger, by the transesterification of vinyltriethoxysilane with 2-methyl-1,3-propanediol.

Into a 500 mL round-bottomed flask equipped with a ten-plate Oldershaw column and distillation head was added 150 grams of vinyltriethoxysilane (Silquest A-151, Momentive Performance Materials Inc.), 149 grams of 2-methyl-1,3-propanediol and 0.15 grams of p-toulenesulfonic acid.

The reaction mixture was stirred with a magnetic stirrer and heated to 55° C. for one hour. The mixture was allowed to cool to 40° C. and then placed under a vacuum of 430 torr to remove evolved ethanol (103.2 grams) which was collected in the receiver. The substantially ethanol-free mixture was neutralized with 0.39 grams of 21 weight percent ethanolic sodium ethoxide solution and filtered.

EXAMPLE 2

This example illustrates the preparation of a silane (a) or mixture thereof, useful as an adhesion promoter, by the transesterification of 3-aminopropyltriethoxysilane with 2-methyl-1,3-propanediol.

Into a 3-liter round-bottomed flask equipped with a 2-inch Vigreaux column and distillation head was added 1222 grams of 3-aminopropyltriethoxysilane (Silquest A-1100, Momentive Performance Materials Inc.), 995 grams of 2-methyl-1,3-propaanediol and 11 grams of 21 weight percent ethanolic sodium ethoxide solution. The mixture was stirred with a magnetic stirrer and heated to 50° C. under a vacuum of 220 torr. Evolved ethanol (738 grams) was collected in the receiver.

EXAMPLE 3 AND 4 AND COMPARATIVE EXAMPLE 1

A moisture curable sealant composition was prepared containing silane (a) of Example 1 as a moisture scavenger (Example 3) and silane (a) of Example 2 as an adhesion promoter (Example 4). For comparison with the silanes from which silanes (a) of Examples 1 and 2 were prepared, a sealant composition was prepared containing vinyltriethoxysilane as a moisture scavenger and 3-aminopropyltriethoxysilane as an adhesion promoter (Comparative Example 1 and 2, respectively).

The base sealant formulation used in Example 3 and 4 and Comparative Example 1 and 2 is set forth in Table 1 as follows:

TABLE 1

| Base Moisture curable Sealant Composition | |
|---|---|
| Component | Weight, g |
| SPUR 1015 LM (Momentive Performance Materials Inc.), moisture curable silylated polyurethane resin | 114.7 |
| diisodecylphthalate (plasticizer) | 91.75 |
| Ultra Pflex (Specialty Minerals Inc.), precipitated calcium carbonate, a filler (0.07 micron) | 165.15 |
| Hi Pflex (Specialty minerals Inc.), precipitate calcium carbonate a filler (3.5 micron) | 110.1 |
| Tinuvin 213 (Ciba Specialty Chemicals), a UV stabilizer | 1.15 |
| Tinuvin 622L (Ciba Specialty Chemicals), a UV stabilizer | 1.15 |
| TS-720 (Degussa) a thixotropic agent | 5.575 |
| Ti Pure (DuPont), titanium dioxide slurry, a pigment | 5.75 |
| Foamrez SUL-4 (Chemtura), dibutyltin dilaurate, a cure catalyst | .015 |

To the foregoing base sealant composition were added the amounts of the silanes indicated in Table 2 as follows:

TABLE 2

Weight of Silane Additive in Formulation

| Example | Silane Additives | Weight, g |
| --- | --- | --- |
| Example 3 | silane (b) of Example 1 as moisture scavenger | 2.75 |
| Example 4 | silane (b) of Example 2 as adhesion promoter | 3.5 |
| Comparative Example 1 | vinyltriethoxysilane as moisture scavenger | 1.7 |
| Comparative Example 1 | 3-aminopropyltriethoxysilane as adhesion promoter | 2.85 |

The preparation of the base sealant composition of Table 1 and the addition thereto of the silanes of Table 2 was as follows (all of the fillers and silica components were used as is without pre-drying):

Step 1: In a one-liter Ross Mixer, add SPUR 1015 LM, silane moisture scavenger, and Tinuvins 213 and 622L and mix for 15 minutes at 38° C. (100° F.).

Step 2: Add silica and mix for 30 minutes under vacuum of 635-711 mm (Hg 25-28 inch Hg).

Step 3: Add half of the calcium carbonate and mix for 1 hour under vacuum. Raise temperature to 93° C. (200° F.).

Step 4: Add the remaining calcium carbonate, plasticizer, and Ti Pure and mix for an additional 1-2 hour under the aforestated vacuum and temperature conditions.

Step 5: Add silane adhesion promoter and mix for 15 min. under the same conditions.

Step 6: Cool to 38° C. (100° F.), then add Foamrez SUL-4 and mix for 15 minutes under vacuum to de-gas.

The effectiveness of the silane moisture scavengers was determined by measuring the moisture content of samples taken at different steps of the preparation of the sealant compositions. The results of the determinations are set forth in Table 3 below:

TABLE 3

Effectiveness of the Silane Moisture Scavengers

| Sealant Composition | Sample Taken | Water, ppm |
| --- | --- | --- |
| Example 3 | During Step 4, following addition of all fillers | 460 |
| | Before Step 5 | 417 |
| | Before Step 6 | 0 |
| Comparative Example 1 | During Step 4, following addition of all fillers | 642 |
| | Before Step 5 | 219 |
| | Before Step 6 | 200 |

These data show that silane (a) of Example 1 performed well as a moisture scavenger with the moisture level decreasing even faster following the addition of silane adhesion promoter in Step 5 of the procedure used for preparing the sealant composition of Example 3 compared with the rate of moisture reduction following addition of silane adhesion promoter in Step 5 of the preparation of the sealant composition of Comparative Example 1.

Mechanical properties of the sealant compositions of Example 3 and Comparative Example 1 following curing for two weeks at 23°/50% relative humidity were measured by ASTM D 412 for tensile strength and elongation and ASTM C661 for hardness. The measurement data are presented in Table 4 as follows:

TABLE 4

Tensile Strength, Elongation and Hardness of cured Sealant Compositions

| Cured Sealant Composition | Tensile Strength (psi) | Young's Modulus (psi) | 100% Modulus (psi) | Elongation (%) | Hardness Shore A |
| --- | --- | --- | --- | --- | --- |
| Example 4 | 243 | 223 | 153 | 305 | 39 |
| Comparative Example 2 | 261 | 149 | 145 | 271 | 36 |

For the evaluation of the adhesion properties of the sealant compositions, the uncured compositions were applied as coatings on each of three substrates, namely, glass, aluminum and polyvinylchloride (PVC), test plates, the coatings were cured for 2 weeks at 23° C./50% relative humidity, the coated test plates were then immersed in water for seven days and thereafter measured for wet adhesion by ASTM C 794. The measurement data are presented in Table 5 as follows:

TABLE 5

Adhesion of Sealant Compositions to Different Substrates

| Cured Sealant Composition | Glass lbs/in (failure) | Aluminum lbs/in (failure) | PVC lbs/in (failure) |
| --- | --- | --- | --- |
| Test Plate of Example 4 | 30.2 (100% CF) | 19.6 (100% CF) | 16.7 (100% CF) |
| Test Plate of Comparative Example 2 | 28.1 (100% CF) | 18.5 (100% CF) | 30.0 (100% CF) |

The test results showed the sealant containing silane Example 2 as adhesion promoter has the mechanical properties and adhesion characteristics essentially to the Comparative Example 2 when loading level based on mole equivalence.

While the process of the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

What is claimed is:

1. A hydrolyzable silane of low VOC-generating potential which possesses:
   (i) at least one organofunctional group, said group being a non-bulky electron-withdrawing group and/or a group which is capable of interacting with a mutually interactive organic resin following contact therewith, the organofunctional group being bonded to a silicon atom of a hydrolyzable silyl group through a stable bridging group, and
   (ii) at least one hydrolyzable group bonded to silicon and containing at least two heteroatoms selected from the group consisting of oxygen, nitrogen and their combinations, hydrolysis of the hydrolyzable group generating a compound having a vapor pressure lower than 0.1 mm Hg at 20° C.; wherein said hydrolysable silane is a monomeric silane of general Formula (1):

$$(X^1{}_a X^2{}_b X^3{}_c SiR^1)_d Z \tag{1}$$

wherein:

each occurrence of $R^1$ is independently a chemical bond between a silicon atom, and a carbon atom of the Z group; a hydrocarbyl group of 1 to 10 carbon atoms; or a heterocarbyl group of 1 to 10 carbon atoms and at least one heteroatom of nitrogen or oxygen;

each occurrence of $X^1$ is a monovalent heterocarbyl group of general Formula (2):

$$(HA^1)_{e-1}R^3(A^2-) \qquad (2)$$

wherein $R^3$ is a hydrocarbyl group of 2 to 8 carbon atoms: each occurrence of $A^1$ and $A^2$ is a heteroatom selected from the group consisting of oxygen and nitrogen of the structure $-NR^4-$ wherein each occurrence of $R^4$ is a hydrogen or an alkyl or aryl group of from 1 to 6 carbon atoms; and e is an integer from 2 to 3; with the provisos that (i) the $A^2$ group is bonded to a carbon atom of $R^3$ and to the silicon atom of Formula (1), (ii) $A^1$ is bonded to $R^3$ and to a hydrogen atom, and (iii) the group $HA^1$- represents a free hydroxyl (—OH) or amino (—$NR^4H$) group and is therefore not covalently bonded directly to the silicon atom;

each occurrence of $X^2$ is a divalent heterocarbyl group of general Formula (3):

$$(HA^3)_{f-2}R^5(A^4-)_2 \qquad (3)$$

wherein $R^5$ is a hydrocarbyl group of 2 to 8 carbon atoms; each occurrence of $A^3$ and $A^4$ is a heteroatom selected from the group consisting of oxygen and substituted nitrogen of the structure $-NR^4-$, wherein each occurrence of $R^4$ is a hydrogen or an alkyl or aryl group of from 1 to 6 carbon atoms; f is an integer from 2 to 3, with the provisos that (i) the two -$A^4$- groups are bonded to two different carbon atom of $R^5$ and to the same silicon atom of Formula (1) to form a cyclic structure, (ii) $A^3$ is bonded to $R^5$ and to a hydrogen atom, and (iii) the group $HA^3$-represents a free hydroxyl (—OH) or amino (—$NR^4H$) groups and is therefore not covalently bonded directly to the silicon atom;

each occurrence of $X^3$ is a trivalent heterocarbyl group of general Formula (4):

$$R^6(A^5-)_3 \qquad (4)$$

wherein $R^6$ is a hydrocarbyl group of 3 to 8 carbon atoms: each occurrence of $A^5$ is a heteroatom selected from the group consisting of oxygen and substituted nitrogen of the structure $-NR^4$- wherein each occurrence of $R^4$ is a hydrogen or an alkyl or aryl group of from 1 to 6 carbon atoms, with the proviso that the three -$A^5$- groups are bonded to three different carbon atoms of $R^6$ and to the same silicon atom of Formula (1) to form a bicyclic structure:

each Z is a monovalent or polyvalent organofunctional group of valence d selected from the group consisting of (a) an amino group of general Formula (5):

$$(-)_gN(R^7)_{3-(g+i)}[-R^8N(R^9)_{2-h}(-)_h]_i \qquad (5)$$

wherein each occurrence of $R^7$ and $R^9$ is independently hydrogen or an alkyl or aryl group of from 1 to 6 carbon atoms; $R^8$ is an alkylene, aralkylene or arylene group of from 2 to 10 carbon atoms; (—) represents the bond between the nitrogen atom and a carbon of the $R^1$ group; each g, h and i are integers wherein g is from 1 to 3, h is from 1 to 2 and i is 0 or 1 with the provisos that (i) g+(i×h)=d; and (ii) when g=3, then i=0, (b) an epoxy group of general Formula (6):

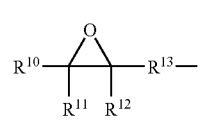

wherein:
each occurrence of $R^{10}$ is independently a hydrogen or an alkyl group containing from 1 to 6 carbon atoms;
each occurrence of is independently a hydrogen or a hydrocarbyl group containing form 1 to 10 carbon atoms and, optionally, at least one oxygen atom, selected from the group consisting of monovalent alkyl, alkenyl, arenyl, aryl and aralkyl groups; divalent alkylene, alkenylene, arenylene, arylene and aralkylene groups in which one carbon atom of $R^{11}$ is covalently bonded to a carbon of the epoxy ring and the same or different carbon atom of $R^{11}$ is covalently bonded to a carbon atom of $R^{12}$ or $R^{13}$ to form a cyclic aliphatic structure; and polyvalent hydrocarbyl in which one carbon atom of $R^{11}$ is covalently bonded to a carbon atom of the epoxy ring and the same and/or different carbon atom of $R^2$ forms at least two covalent bonds with carbon atoms of $R^{12}$ or $R^{13}$ or at least one covalent bond with both $R^{12}$ and $R^{13}$ to form a bicyclic or a polycyclic aliphatic structure;
each occurrence of $R^{12}$ is independently a hydrogen or a hydrocarbyl group containing from 1 to 10 carbon atoms and, optionally, at least one oxygen atom, selected from the group consisting of monovalent alkyl, alkenyl, arenyl, aryl and aralkyl groups; divalent alkylene, alkenylene, arenylene, arylene and aralkylene groups in which one carbon atom of $R^{12}$ is covalently bonded to a carbon atom of the epoxy ring and the same or different carbon atom of $R^{12}$ is covalently bonded to a carbon atom of $R^{11}$or $R^{13}$ to form a cyclic aliphatic structure; and polyvalent hydrocarbyl in which one carbon atom of $R^{12}$ is covalently bonded to a carbon atom of the epoxy ring and the same and/or different carbon atoms of $R^{12}$ form at least two covalent bonds with $R^{11}$ or $R^{13}$ or at least one covalent bond with both $R^{11}$ and $R^{13}$ to form a bicyclic or a polycyclic aliphatic structure;
each occurrence of $R^{13}$ is independently a chemical bond between the epoxy ring and $R^1$; a divalent or polyvalent hydrocarbyl group containing up to 12 carbon atoms selected from the group consisting of divalent alkylene, aralkylene, arenylene, arylene and aralkylene groups linking the epoxy group to $R^1$ and, optionally, at least one oxygen atom; and polyvalent hydrocarbyl group in which one carbon atom of $R^{13}$ forms a covalent bond with the carbon atom of the epoxy ring, the same or different carbon atom of $R^{13}$ forms a bond with a carbon atom of $R^1$, and the same or different carbon atom of $R^{13}$ firms at least one covalent bond with a carbon atom of $R^{11}$ or $R^{12}$ to form a bicyclic or a polycyclic structure.

(c) a ureido group of general Formula (7):

$$(-)_jN(R^{14})_{2-j}C(=O)N(R^{15})_{2-k}(-)_k \qquad (7)$$

wherein each occurrence of $R^{14}$ and $R^{15}$ is independently a hydrogen or an alkyl or aryl group of from 1 to 6 carbon atoms; (—) represents the bond between the nitrogen atom and a carbon of the $R^1$ group; j and k are an integers wherein j is from 1 to 2, k is from 0 to 2 with the proviso that j+k=d.

(d) an alkenyl group of general Formula (8):

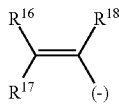

wherein each occurrence of $R^{16}$, $R^{17}$ and $R^{18}$ is independently a hydrogen or an alkyl or aryl group of from 1 to 6 carbon atoms; and (—) represents the bond between the unsaturated carbon atom and a carbon of the $R^1$ group or the silicon atom, and (e) a carbamato group of general Formula (9)

$$R^{19}OC(=O)NH— \quad (9)$$

wherein:
$R^{19}$ is a hydrocarbyl group of from 1 to 8 carbon atoms; and each occurrence of a, b, c and d are integers, wherein a is 0 to 3; b is 0 or 1; c is 0 or 1; and d is 1 to 4; with the proviso that when c is 0, then a+2b=3 and when b is 1, then a=1 and c=0.

2. A hydrolyzable silane of low VOC-generating potential which possesses:

(i) at least one organofunctional group, said group being a non-bulky electron-withdrawing group and/or a group which is capable of interacting with a mutually interactive organic resin following contact therewith, the organofunctional group being bonded to a silicon atom of a hydrolyzable silyl group through a stable bridging group, and (ii) at least one hydrolyzable group bonded to silicon and containing at least two heteroatoms selected from the group consisting of oxygen, nitrogen and their combinations, hydrolysis of the hydrolyzable group generating a compound having a vapor pressure lower than 0.1 mm Hg at 20° C.;

wherein said hydrolysable silane is at least one oligomeric silane of general Formula (10):

$$[(X^1_a X^2_b X^b_n SiR^1)_d Z]_m \quad (10)$$

wherein:
each occurrence of $R^1$ is independently a chemical bond between a silicon atom and a carbon atom of the Z group; a hydrocarbyl group of to 10 carbon atoms; or a hetero-carbyl group of 1 to 10 carbon atoms and at least one heteroatom of nitrogen or oxygen:

each occurrence of $X^1$ is $R^2$ wherein $R^2$ is a monovalent heterocarbyl group of general Formula (2):

$$(HA^1)_{e-1}R^3(A^2-) \quad (2)$$

wherein $R^3$ is a hydrocarbyl group of 2 to 8 carbon atoms; each occurrence of $A^1$ and $A^2$ is a heteroatom selected from the group consisting of oxygen and nitrogen of the structure —$NR^4$— wherein each occurrence of $R^4$ is a hydrogen or an ally or aryl group of from 1 to 6 carbon atoms; and e is an integer from 2 to 3; with the provisos that (i) the $A^2$ group is bonded to a carbon atom of $R^3$ and to the silicon atom of Formula (1), (ii) $A^1$ is bonded to $R^3$ and to a hydrogen atom, and (iii) the group $HA^1$- represents a free hydroxyl (—OH) or amino (—$NR^4H$) group and is therefore not covalently bonded directly to the silicon atom;

each occurrence of $X^2$ is a divalent heterocarbyl group of general Formula (3):

$$(HA^3)_{f-2}R^5(A^4-)_2 \quad (3)$$

wherein $R^5$ is a hydrocarbyl group of 2 to 8 carbon atoms; each occurrence of $A^3$ and $A^4$ is a heteroatom selected from the group consisting of oxygen and substituted nitrogen of the structure —$NR^4$—, wherein each occurrence of $R^4$ is a hydrogen or an alkyl or aryl group of from 1 to 6 carbon atoms; f is an integer from 2 to 3, with the provisos that (i) the two -$A^4$- groups are bonded to two different carbon atom of $R^5$ and to the same silicon atom of Formula (1) to form a cyclic structure, (ii) $A^3$ is bonded to $R^5$ and to a hydrogen atom, and (iii) the group $HA^3$- represents a free hydroxyl (—OH) or amino (—$NR^4H$) groups and is therefore not covalently bonded directly to the silicon atom;

each occurrence of $X^b$ is independently at least a divalent heterocarbyl group of general Formula (11):

$$(HA^6)_{2-o}R^{20}(A^7-)(A^8-)_o \quad (II)$$

wherein:
$R^{20}$ is a hydrocarbyl group of 2 to 8 carbon atoms; each occurrence of $A^6$, $A^7$ and $A^8$ is a heteroatom selected from the group consisting of oxygen and substituted nitrogen of the structure —$NR^4$— wherein each occurrence of $R^4$ is hydrogen or an alkyl or aryl group of from 1 to 6 carbon atoms; and o is an integer from 1 to 2, with the proviso that $A^7$ and $A^8$ are bonded to different carbon atoms of $R^{20}$ and to silicon atoms on different monomer units;

each Z is a monovalent or polyvalent organofunctional group of valence d selected from the group consisting of amino, epoxy, ureido and alkenyl groups; and, each occurrence of a, b, d, n and n is independently an integer, wherein a is 0 to 2; b is 0 or 1; d is 1 to 4; m is 2 to 10; and n is 1 to 3; with the proviso that when b is 1, then a is 0 and n is 1.

3. The hydrolyzable silane of claim 1, wherein:
$R^1$ is a straight chain alkylene group of from 1 to 3 carbon atoms;
$R^3$ is a hydrocarbyl group of 3 to 6 carbon atoms;
each occurrence of $A^1$ and $A^2$ is oxygen;
$R^5$ is a hydrocarbyl group of 3 to 6 carbon atoms;
each occurrence of $A^3$ and $A^4$ is oxygen;
$R^6$ is a hydrocarbyl group of 3 to 6 carbon atoms;
each occurrence of $A^5$ is oxygen;
Z is —$NH_2$, —$NHR^8NH_2$ wherein $R^8$ is ethylene, propylene or butylene, —$NHC(=O)NH_2$ or glycidoxy; and, d is 1.

4. The hydrolyzable silane of claim 1 which is at least one silane selected from the group consisting of
3-(2-aminomethyl-5-methyl-[1,3,2]dioxasilinan-2-yloxy)-2-methyl-propan-1-ol;
3-(2-aminopropyl -5-methyl-[1,3,2]dioxasilinan-2-yloxy)-2-methyl-propan-1-ol;
4-[2-(3-amino-propyl)-4,4,6-trimethyl-[1,3,2]dioxasilinan-2-yloxy]-2-methyl-pentan-2-ol;
3-{2-[3-(2-amino-ethylamino)-propyl]-4-methyl-[1,3,2]dioxasilinan-2-yloxy}butan-1-ol;
{3-[2-(3-hydroxy-1-methyl-propoxy)-4-methyl-[1,3,2]dioxasilinan-2-yl]-propyl}-urea;
[2-(3-hydroxy-2-methyl-propoxy)-5-methyl-[1,3,2]dioxasilinan-2-ylmethyl]-urea;
2-methyl-3-(5-methyl-2-vinyl-[1,3,2]dioxasilinan-2-yloxy)-propan-1-ol;
2-methyl-acrylic acid 2-[2-(3-hydroxy-2-methyl-propoxy)-5-methyl-[1,3,2]dioxasilinan-2-yl]-ethyl ester;
2-methyl-3-[5-methyl-2-(2-oxiranylmethoxy-ethyl)-[1,3,2]dioxasilinan-2-yloxy]-propan-1-ol; and,
2-[5-methyl-2-(6-methyl-5-methylene-hept-6-enyl)-[1,3,2]dioxasilinan-yloxy]-propan-1-ol.

5. A resinous composition of low VOC-generating potential which comprises:
   a) the hydrolyzable silane of claim 2, and
   b) at least one organic resin which is interactive with organofunctional group (i) of said hydrolysable silane.

6. The resinous composition of claim 5 which is formulated as a moisture curable adhesive, coating or sealant.

7. The resinous composition of claim 5 wherein hydrolyzable silane (a) is monomeric, oligomeric or a mixture of both types of silanes.

8. The resinous composition claim 5, wherein:
   $R^1$ of formula (10) is a straight chain alkylene group of from 1 to 3 carbon atoms;
   $R^3$ of formula (2) is a hydrocarbyl group of 3 to 6 carbon atoms;
   each occurrence of $A^1$ and $A^2$ is oxygen and e is 2;
   $R^5$ of formula (3) is a hydrocarbyl group of 3 to 6 carbon atoms;
   each occurrence of $A^3$ and $A^4$ is oxygen and f is 3;
   Z is —$NH_2$, —$NHR^8NH_2$ wherein $R^8$ is ethylene, propylene or butylene, —NHC(=O)$NH_2$ or glycidoxy: and, d is 1.

9. A resinous composition comprising a hydrolyzable silane selected from the group consisting of
   3-(2-aminomethyl-5-methyl-[1,3,2]dioxasilinan-2-methyl-propan-1-ol;
   3-(2-aminopropyl-5-methyl-[1,3,2]dioxasilinan-2-yloxy)-2-methyl-propan-1-ol;
   4-[2-(3-amino-propyl)-4,4,6-trimethyl-[1,3,2]dioxasilinan-2-yloxy]-2-methyl-pentan-2-ol;
   3-{2-[3-(2-amino-ethylamino)-propyl]-4-methyl-[1,3,2]dioxasilinan-2-yloxy}-butan-1-ol;
   {3-[2-(3-hydroxy-1-methyl-propoxy)-4-methyl-[1,3,2]dioxasilinan-2-yl]-propyl}-urea;
   [2-(3-hydroxy-2-methyl-propoxy)-5-methyl-[1,3,2]dioxasilinan-2-ylmethyl]-urea;
   2-methyl-3-(5-methyl-2-vinyl-[1,3,2]dioxasilinan-2-yloxy)-propan-1-ol;
   2-methyl-acrylic acid 2-[2-(3-hydroxy-2-methyl-propoxy)-5-methyl-[1,3,2]dioxasilinan-2-yl]-ethyl ester:
   2-methyl-3-[5-methyl-2-(2-oxiranylmethoxy-ethyl)-[1,3,2]dioxasilinan-2-yloxy]-propan-1-ol; and,
   2-[5-methyl-2-(6-methyl-5-methylene-hept-6-enyl)-[1,3,2]dioxasilinan-2-yloxy]-propan-1-ol.

10. The resinous composition of claim 5 containing at least one additional component selected from the group consisting of filler, plasticizer, thixotropic agent, stabilizer, cure catalyst, solvent, colorant, surfactant and biocide.

11. The moisture cured resinous composition of claim 5.

12. The resinous composition of claim 5 wherein mutually interactive organic resin (b) is at least one resin possessing one or more organofunctional groups selected from the group consisting of hydroxyl, carboxyl, isocyanato, thioisocyanato, carbamato ureido, amido, halo, epoxy, episulfide, amino, mercapto and hydrolyzable silyl.

13. The resinous composition of claim 12 wherein mutually interactive organic resin (b) is at least one resin selected from the group consisting of phenolic, epoxy, polyester, polyamide, polyurethane, polyphenylene sulfide, polycarbonate, polyacrylate, polymethacrylate, polyvinyl alcohol, polyacrylamide, polymethacrylamide, polyvinyl chloride, polyvinylidene chloride, silane-terminated polyol, silane-terminated polyurethane, silylated polyolefin and polystyrene resins and resins obtained from the copolymerization of two or more ethylenically unsaturated monomers.

14. The resinous composition of claim 8 wherein mutually interactive organic resin (b) is at least one resin possessing one or more organofunctional groups selected from the group consisting of hydroxyl, carboxyl, isocyanato, thioisocyanato, carbamato, ureido, amido, halo, epoxy, episulfide, amino, mercapto and hydrolyzable silyl.

15. The resinous composition of claim 14 wherein mutually interactive organic resin (b) is at least one resin selected from the group consisting of phenolic, epoxy, polyester, polyamide, polyurethane, polyphenylene sulfide, polycarbonate, polyacrylate, polymethacrylate, polyvinyl alcohol, polyacrylamide, polymethacrylamide, polyvinyl chloride, polyvinylidene chloride, silane-terminated polyol, silane-terminated polyurethane, silylated polyolefin and polystyrene resins and resins obtained from the copolymerization of two or more ethylenically unsaturated monomers.

16. The resinous composition of claim 9 wherein mutually interactive organic resin (b) is at least one resin possessing one or more organofunctional groups selected from the group consisting of hydroxyl, carboxyl; isocyanato, thioisocyanato, carbamato, ureido, amido, halo, epoxy, episulfide, amino, mercapto and hydrolyzable silyl.

17. The resinous composition of claim 16 wherein mutually interactive organic resin (b) is at least one resin selected from the group consisting of phenolic, epoxy, polyester, polyamide, polyurethane, polyphenylene sulfide, polycarbonate, polyacrylate, polymethacrylate, polyvinyl alcohol, polyacrylamide, polymethacrylamide, polyvinyl chloride, polyvinylidene chloride, silane-terminated polyol, silane-terminated polyurethane, silylated polyolefin and polystyrene resins and resins obtained from the copolymerization of two or more ethylenically unsaturated monomers.

18. The hydrolyzable silane of claim 2 which is at least one silane selected from the group consisting of:
   C-{2-[3-(2-aminomethyl-5-methyl-[1,3,2]dioxasilinan-2-yloxy)-2-methyl-propoxy]-5-methyl-[1,3,2]dioxasilinan-2-yl}-methylamine,
   3-(2-{3-[2-(3-amino-propyl)-5-methyl-[1,3,2]dioxasilinan-2-yloxy]-2-methyl-propoxy}-5-methyl-[1,3,2]dioxasilinan-2-yl)-propylamine, and
   [3-(5-methyl-2-{2-methyl-3-[5-methyl-2-(3-ureido-propyl)-[1,3,2]dioxasilinan-2-yloxy]-propoxy}-[1,3,2]dioxasilinan-2-yl)-propyl]-urea.

19. A resinous composition of low VOC-generating potential which comprises:
   a) the hydrolyzable silane of claim 1, and
   b) at least one organic resin which is interactive with organofunctional group (i) of said hydrolysable silane.

* * * * *